US008920875B2

(12) United States Patent
Suzuki et al.

(10) Patent No.: US 8,920,875 B2
(45) Date of Patent: Dec. 30, 2014

(54) CYCLOOCTATETRAENETRICARBONYL RUTHENIUM COMPLEX, METHOD OF PRODUCING THE SAME, AND METHOD OF PRODUCING FILM USING THE COMPLEX AS RAW MATERIAL

(75) Inventors: Kazuharu Suzuki, Ibaraki (JP); Masayuki Saito, Ibaraki (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 230 days.

(21) Appl. No.: 13/146,420

(22) PCT Filed: Jan. 8, 2010

(86) PCT No.: PCT/JP2010/050127
  § 371 (c)(1),
  (2), (4) Date: Jul. 27, 2011

(87) PCT Pub. No.: WO2010/087217
  PCT Pub. Date: Aug. 5, 2010

(65) Prior Publication Data
  US 2011/0287175 A1  Nov. 24, 2011

(30) Foreign Application Priority Data

Jan. 30, 2009 (JP) ................. 2009-019426

(51) Int. Cl.
  *C23C 16/00* (2006.01)
  *C23C 16/18* (2006.01)
  *H01L 21/28* (2006.01)
  *H01L 21/285* (2006.01)
  *H01L 49/02* (2006.01)
  *C07F 15/00* (2006.01)

(52) U.S. Cl.
  CPC ............. *C07F 15/0046* (2013.01); *C23C 16/18* (2013.01); *H01L 21/28194* (2013.01); *H01L 21/28556* (2013.01); *H01L 28/65* (2013.01)
  USPC .......... 427/248.1; 427/250; 556/136

(58) Field of Classification Search
  USPC ................ 427/248.1, 250; 556/136
  See application file for complete search history.

(56) References Cited

U.S. PATENT DOCUMENTS

| 3,077,489 | A | * | 2/1963 | Coffield et al. ................ 556/142 |
| 2003/0008157 | A1 | | 1/2003 | Shiho et al. |
| 2006/0240190 | A1 | | 10/2006 | Sakai et al. |

FOREIGN PATENT DOCUMENTS

| EP | 2392578 A1 | 12/2011 |
| JP | 2002-201162 A | 7/2002 |

(Continued)

OTHER PUBLICATIONS

Knolker. Efficient Synthesis of Tricarbonyliron-diene complexes—development of an assymetric catalytic complexation, Chem. Rev. 2000, 100, pp. 2941-2961.*

(Continued)

*Primary Examiner* — Kelly M Gambetta
(74) *Attorney, Agent, or Firm* — McDermott Will & Emery LLP

(57) ABSTRACT

To provide a ruthenium compound suitable for a chemical vapor deposition method (CVD method). A liquid cyclooctatetraenetricarbonyl ruthenium complex represented by the following Formula (1) is obtained by irradiating a solution mixture of dodecacarbonyl triruthenium and a cyclooctatetraene with light.

[Formula 7]

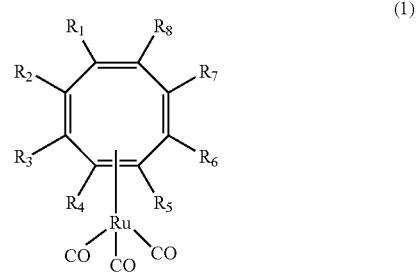

A satisfactory ruthenium film or ruthenium oxide film can be easily obtained by a chemical vapor deposition method using the complex as a raw material.

12 Claims, 1 Drawing Sheet

(56) References Cited

FOREIGN PATENT DOCUMENTS

| JP | 2002-212112 A | 7/2002 |
|----|---------------|--------|
| JP | 2005-60814 A | 3/2005 |
| WO | WO 02/32839 A1 | 4/2002 |

OTHER PUBLICATIONS

Johnson et al. Some reactions of triruthenium dodecacarbonyl, Nature, Mar. 4, 1967, pp. 901-902.*

Extended European Search Report for EP 10 73 5687, which was mailed on Apr. 25, 2012.

H. Li, et al., Vapor Deposition of Ruthenium from an Amidinate Precursor, Journal of the Electrochemical Society, 154 (12), pp. D642-D647, 2007.

H. Li, et al., Synthesis and Characterization of Ruthenium Amidinate Complexes as Precursors for Vapor Deposition, The Open Inorganic Chemistry Journal, 2008, vol. 2, pp. 11-17.

A. C. Cope, et al., Cyclic Polyolefins. XIX. Chloro- and Bromocyclooctatetraenes, Journal of the American Chemical Society, vol. 74, No. 1, Jan. 5, 1952, pp. 168-172.

A. C. Cope, et al., Cyclic Polyolefins. XX. Cyclooctatetraenecarboxylic Acid, Journal of the American Chemical Society, vol. 74, No. 1, Jan. 5, 1952, pp. 173-175.

L. A. Paquette, et al., Homotropylium Cations. Substituent Control on Their Generation and Subsequent Reactions, Journal of the American Chemical Society, vol. 91, No. 17, Aug. 13, 1969.

A. C. Cope, et al., Cyclic Polyolefins. XXI. Alkylcyclooctatetraenes and Alkylcyclooctatrienes from Cyclooctatetraene and Alkyllithium Compounds, Journal of the American Chemical Society, vol. 74, No. 1, Jan. 5, 1952, pp. 175-179.

N. G. Connelly, et al., Stereo- and Regio-Specific C-C Bond Formation via the Coupling of Electrophilic and Nucleophilic Organotransition-Metal Complexes: the X-Ray Crystal Structure of [Ru(CO)2(PPh3)(n2, n3-C8H8R)] [PF6] 0.5CH2Cl2(R=CH2C(Me)=CH2), Journal of Organometallic Chemistry, vol. 299, 1986, pp. C51-C55.

* cited by examiner

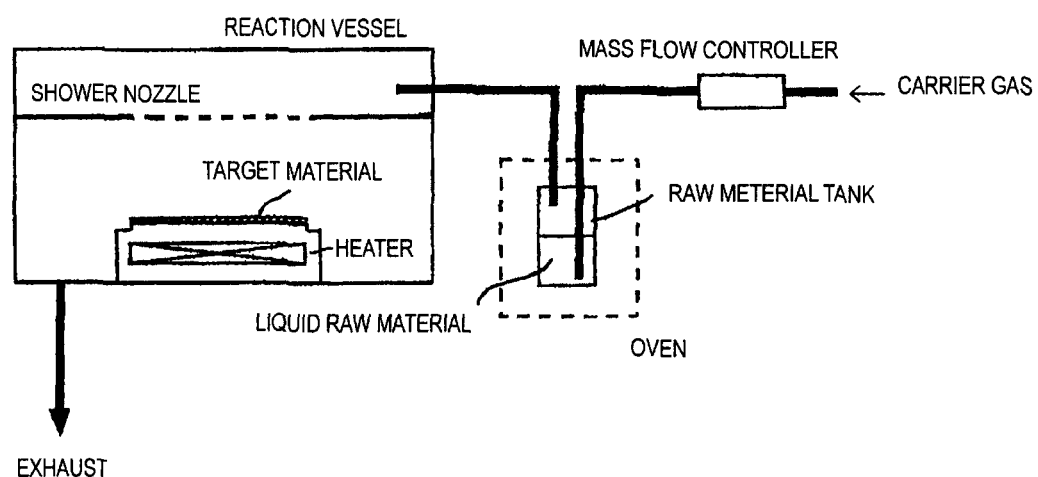

CYCLOOCTATETRAENETRICARBONYL RUTHENIUM COMPLEX, METHOD OF PRODUCING THE SAME, AND METHOD OF PRODUCING FILM USING THE COMPLEX AS RAW MATERIAL

CROSS REFERENCE TO PRIOR APPLICATIONS

This application is a U.S. National Phase application under 35 U.S.C. § 371 of International Application No, PCT/JP2010/050127, filed on Jan. 8, 2010 and claims benefit of priority to Japanese Patent Application No. 2009-019426, filed on Jan. 30, 2009. The International Application was published in Japanese on Aug. 5, 2010 as WO 2010/087217 A1 under PCT Article 21(2). All of these applications are herein incorporated by reference.

TECHNICAL FIELD

The present invention relates to a ruthenium complex suitable for a chemical vapor deposition method (CVD method), a method of producing the complex, and a method of producing a ruthenium film or a ruthenium oxide film using the complex as a raw material.

BACKGROUND ART

A dynamic random access memory (DRAM) is used as the memory device of a computer. Progress has been made in the size reduction and integration of the devices with the improvement in performance. At present, highly dielectric materials and electrode materials, which are important for promoting integration, are being developed.

When a dielectric layer such as a silicon oxide substrate and an electrode layer of, for example, copper or silver are laminated to each other, in order to prevent mutual bleeding of the materials from both layer, an iridium film or a platinum film is disposed as an intermediate layer. However, iridium is expensive, and platinum is difficult to etch, making it difficult to form an electrode structure. Accordingly, a ruthenium film and a ruthenium oxide film, which are inexpensive and easy to etch, are expected as intermediate layer suitable for DRAMs. Furthermore, in order to correspond to miniaturization of device structure with the improvement in performance of the DRAM, a film-forming process by a CVD method, instead of conventional sputtering, and development of a ruthenium material therefor are expected.

A liquid material is superior to a solid material for producing an excellent film by the CVD method. When a solid is used as a raw material, the composition of gaseous phase is heterogenous, preventing the thickness of a deposited film from being uniform. On the other hand, when a liquid is used as a raw material, the composition of gaseous phase is homogenous, allowing the thickness of a deposited film to be uniform. Since a precise supply of a raw material is possible by using a liquid as raw material and using a mass flow controller, film-forming conditions can be strictly controlled to more precisely control the thickness.

FIG. 1 shows a schematic diagram illustrating a bubbler method using a mass flow controller, as an example of the CVD method.

As ruthenium-containing CVD materials, for example, cyclopentadienyl-based materials, such as biscyclopentadienyl ruthenium and bisethylcyclopentadienyl ruthenium, and ruthenium complexes having amidinium as the ligands have been reported.

Since the biscyclopentadienyl ruthenium is a solid at room temperature, it is necessary to use a sublimation method for vaporizing it, and it is difficult to stably supply a sufficient amount of its vapor with high accuracy.

The bisethylcyclopentadienyl ruthenium is a liquid at room temperature and is possible to perform mass flow control by, for example, a bubbler method. However, high step coverage has not been obtained in a film-forming test using the CVD method. Furthermore, the material is unstable against air and therefore has a problem of difficulty in handling.

The ruthenium complex having amidinium as the ligand has been reported as a ruthenium complex showing high step coverage. It is reported that a ruthenium thin film can be uniformly formed down to the terminal portion of a fine pore with a radius of 200 nm and a depth of 8000 nm (aspect ratio: 40) by using this compound (see Non Patent Literature 1), and this is attracting attention as a material that can be applied to a process of producing an electrode of a DRAM/capacitor portion having a complicated structure. However, this compound is a solid at ordinary temperature and has a high boiling point of 203 to 205° C. (see Non Patent Literature 2). Therefore, a vaporizer for liquid cannot be used for forming a film by this compound.

CITATION LIST

Patent Literature

PTL 1: JP-A-2002-201162
PTL 2: JP-A-2002-212112
PTL 3: JP-A-2005-60814

Non Patent Literature

NPL 1: H. Li, et al., Journal of the Electrochemical Society, vol. 154, pp. D642-D647, 2007
NPL 2: H. Li, et al., The Open Inorganic Chemistry Journal, vol. 2, pp. 11-17, 2008
NPL 3: A. C. Cope, et al., Journal of the American Chemical Society, vol. 74, p. 168, 1952
NPL 4: A. C. Cope, et al., Journal of the American Chemical Society, vol. 74, p. 173, 1952
NPL 5: L. A. Paquette, et al., Journal of the American Chemical Society, vol. 91, p. 4714, 1969
NPL 6: A. C. Cope, et al., Journal of the American Chemical Society, vol. 74, p. 175, 1952

SUMMARY OF INVENTION

Technical Problem

It is an object of the present invention to provide a liquid ruthenium compound that is suitable for producing a film by a CVD method.

Solution to Problem

The present inventors have found the fact that the above-described problems can be solved by a cyclooctatetraenetricarbonyl ruthenium complex having an alkyl group and represented by the following General Formula (1):

[Formula 1]

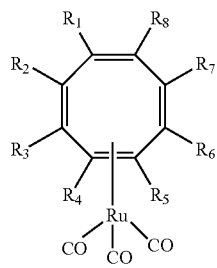

(1)

(in the formula, one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms; and the total number of carbon atoms of the alkyl group or groups is 6 or less).

The one or two alkyl group or groups each having 1 to 6 carbon atoms is or are bound to the cyclooctatetraene ligand of the cyclooctatetraenetricarbonyl ruthenium complex of the present invention. When two alkyl groups each having 1 to 6 carbon atoms are bound, these alkyl groups may be the same as or different from each other, and the total number of carbon atoms of the alkyl groups is 6 or less.

The alkyl group having 1 to 6 carbon atoms as $R_1$, $R_2$, $R_3$, $R_4$, $R_5$, $R_6$, $R_7$, or $R_8$ in the cyclooctatetraenetricarbonyl ruthenium complex of the present invention may be a linear or branched alkyl group. Since an alkyl group having a long carbon chain tends to increase boiling point and decrease vapor pressure, an alkyl group having a short carbon chain, i.e., ethyl, methyl, propyl, isopropyl, butyl, or isobutyl group, is preferably used. In particular, a methyl group or an ethyl group is more preferred. When the number of the alkyl groups is two, combinations of $R_1$ and $R_2$, $R_1$ and $R_3$, and $R_1$ and $R_4$ are preferred. The number of the alkyl group is preferably one, and the alkyl group is most preferably a methyl group or an ethyl group.

The cyclooctatetraenetricarbonyl ruthenium complex of the present invention is a liquid at 0° C., and, therefore, a CVD method using a liquid as a raw material can be employed. Since the complex is a liquid, the composition of its gaseous phase is homogenous, allowing a deposited film to have a uniform thickness. Since a precise supply of the raw material is possible by using a mass flow controller, film-forming conditions can be strictly controlled to more precisely control the thickness.

The cyclooctatetraenetricarbonyl ruthenium complex of the present invention is stable in air and also has a high vapor pressure. Therefore, the ruthenium complex can be easily vaporized and is also stable even in the vaporized state. In addition, the ruthenium complex is easily decomposed by, for example, heat to deposit ruthenium metal on a target material. On this occasion, ruthenium oxide can be easily deposited by performing the deposition under an atmosphere containing oxygen.

The unsubstituted cyclooctatetraenetricarbonyl ruthenium complex is a solid, and when the CVD method is performed using it as a raw material, the gaseous phase is heterogenous, preventing the thickness of a deposited film from being uniform.

The cyclooctatetraenetricarbonyl ruthenium complex of the present invention can be produced by irradiating a solution mixture of dodecacarbonyl triruthenium represented by the following Formula (2) and a cyclooctatetraene represented by the following Formula (3) with light having a wavelength of 300 to 850 nm. In particular, high energy light having a wavelength of 300 to 600 nm can accelerate the reaction and is therefore preferred. It is conceivable that the carbonyl group is eliminated by irradiation of the dodecacarbonyl triruthenium with light and, instead, the cyclooctatetraene represented by the Formula (3) coordinates to generate the cyclooctatetraenetricarbonyl ruthenium complex of the present invention.

[Formula 2]

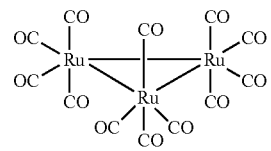

(2)

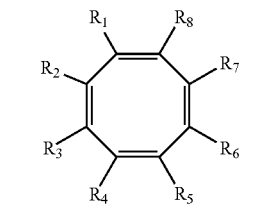

(3)

(In the formula, one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms; and the total number of carbon atoms of the alkyl group or groups is 6 or less.)

The light irradiation is performed in a solvent. Any solvent that can dissolve both the dodecacarbonyl triruthenium serving as a raw material and the cyclooctatetraene serving as a ligand and does not react with them can be used. Preferred examples of the solvent include saturated hydrocarbons having 1 to 12 carbon atoms, cyclic saturated hydrocarbons, benzene, toluene, and xylene. The solvents may be used alone or as a solvent mixture of two or more. Among the above-mentioned solvents, hexane and cyclohexane are preferred, since they are inexpensive and function as purely solvents not having a function as a ligand.

The solution temperature during the light irradiation reaction is preferably from 0 to 100° C., more preferably from 20 to 60° C. Even if the temperature is lower than 0° C., the reaction proceeds, but the reaction rate is impractically slow. On the other hand, if the temperature is higher than 60° C., the product is thermally decomposed, or a side reaction proceeds, resulting in a decrease in yield of the target compound.

After the completion of the reaction, the product may be isolated by any method without particular limitation. As a general method, the precipitated solid is removed by filtration, and the solvent and the unreacted ligand are distilled away from the obtained solution. The soluble component is collected with a solvent such as hexane, and the target ruthenium compound can be obtained by distilling away the hexane. In the case of conducting further purification, a saturated solution is produced at room temperature using a saturated hydrocarbon solvent such as hexane and is then cooled to recrystallize. Alternatively, distillation or sublimation may be performed by heating in vacuum.

In order to produce a ruthenium film or a ruthenium oxide film using the ruthenium complex of the present invention as a raw material, a CVD method can be employed. That is, the film is produced by vaporizing the ruthenium complex, transporting the vapor on a target material, and thermally decomposing the ruthenium complex on the target material. A ruthenium film can be produced in an atmosphere not containing oxygen, and a ruthenium oxide film can be produced in an atmosphere containing oxygen.

The ruthenium complex can be vaporized by any appropriate method. The CVD method usually employs a system of letting a raw material stored in a raw material container bubble while heating or a system of heating and vaporizing a raw material stored in a raw material container with a vaporizer but in the ruthenium complex of the present invention, any system can be employed. The heating temperature for vaporizing the ruthenium complex is preferably from 10 to 150° C. at which the ruthenium complex raw material is not thermally decomposed. More preferred vaporization temperature is from 20 to 120° C.

The ruthenium complex can be decomposed by heating the target material in a range of 150 to 500° C., more preferably in a range of 200 to 400° C.

By maintaining the inside of a reaction vessel at a reduced pressure atmosphere of 5 to 10000 Pa, excessive heating for vaporizing a raw material is unnecessary. Therefore, thermal decomposition is inhibited, and a satisfactorily uniform thickness distribution can be obtained. The more preferred pressure range inside the reaction vessel is from 10 to 2000 Pa.

By the above-described CVD method, a ruthenium film or a ruthenium oxide film having a uniform thickness can be formed on a target material.

Advantageous Effects of Invention

Since the ruthenium complex of the present invention is a liquid, the thickness of a deposited film can be made uniform. In addition, since a precise supply of a raw material and strict control of film-forming conditions are possible by using a mass flow controller, the thickness can be more precisely controlled. Furthermore, since the ruthenium complex is stable in air, easily vaporized, stable in a gaseous state, and easily decomposed by heat, an effect of easily producing a ruthenium film or a ruthenium oxide film on a target material is achieved.

Accordingly, capacitors contained in a DRAM can be further miniaturized, resulting in increases in density and performance of memory devices of the DRAM.

BRIEF DESCRIPTION OF DRAWINGS

FIG. 1 is a schematic diagram of a bubbler method using a mass flow controller.

DESCRIPTION OF EMBODIMENTS

EXAMPLES

Example 1

Synthesis of Methylcyclooctatetraenetricarbonyl Ruthenium

Dodecacarbonyl triruthenium (0.24 g (0.375 mmol), manufactured by Tanaka Kikinzoku Kogyo K.K.) and methyl cyclooctatetraene (1.2 g (10.15 mmol), see NPL 3, NPL 4, and NPL 5) were dissolved in cyclohexane. After deoxidation of the resulting solution, the solution was irradiated with light using a Deep UV lamp (manufactured by Ushio Inc., SX-U1502MQQ) for 72 hours with stirring. After the completion of the light irradiation, solid precipitate was removed from the reaction mixture by filtration, and the filtrate was collected. The filtrate was concentrated under reduced pressure and was purified by column chromatography using hexane as a developing solvent and alumina (manufactured by Wako Pure Chemical Industries, Ltd.) as a filler. The column eluate was concentrated under reduced pressure to obtain a yellow liquid of a target methylcyclooctatetraenetricarbonyl ruthenium. Amount of the product: 57.3 mg (yield: 17%), vapor pressure (23° C.): 38 to 42 Pa, 1H-NMR (CDCl$_3$) δ (ppm): 5.86 (t, J=10 Hz, 2H, —Hb), 5.55 (t, J=10 Hz, 1H, —Hd), 5.12 (t, J=10 Hz, 2H, —Hc), 4.71 (d, J=10 Hz, 2H, —Ha), 1.92 (s, 3H, CH$_3$—), and IR (KBr, cm$^{-1}$): 2065, 1997.

In the above-mentioned NMR spectrum, Ha to Hd are those shown in the following formula:

[Formula 3]

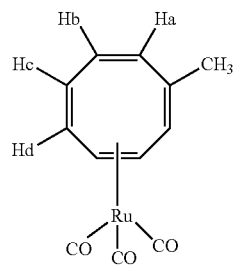

The obtained methylcyclooctatetraenetricarbonyl ruthenium was not solidified even by cooling to −20° C.

Example 2

Synthesis of Ethylcyclooctatetraenetricarbonyl Ruthenium

Dodecacarbonyl triruthenium (0.24 g (0.375 mmol), manufactured by Tanaka Kikinzoku Kogyo K.K.) and ethyl cyclooctatetraene (1.22 g (9.23 mmol)) were dissolved in 6 mL of cyclohexane. After deoxidation of the resulting solution, the solution was irradiated with light using a Deep UV lamp (manufactured by Ushio Inc., SX-U1502MQQ) for 72 hours with stirring. After the completion of the light irradiation, solid precipitate was removed from the reaction mixture by filtration, and the filtrate was collected. The filtrate was concentrated under reduced pressure and was purified by column chromatography using hexane as a developing solvent and alumina (manufactured by Wako Pure Chemical Industries, Ltd.) as a filler. The column eluate was concentrated under reduced pressure to obtain a brown liquid of a target ethylcyclooctatetraenetricarbonyl ruthenium. Amount of the product: 21.7 mg (yield: 7%), vapor pressure (23° C.): 37 to 39 Pa, 1H-NMR (400 MHz, CDCl$_3$) δ (ppm): 5.90 (t, J=10 Hz, 2H, —Hb), 5.61 (t, J=10 Hz, 1H, —Hd), 5.13 (t, J=10 Hz, 2H, —Hc), 4.62 (d, J=10 Hz, 2H, —Ha), 2.12 (q, J=7 Hz, 2H, —CH$_2$—), 1.07 (t, J=7 Hz, 3H, CH$_3$—), and IR (KBr, cm$^{-1}$): 2062, 1987.

In the above-mentioned NMR spectrum, Ha to Hd are those shown in the following formula:

[Formula 4]

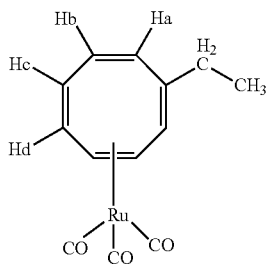

The obtained ethylcyclooctatetraenetricarbonyl ruthenium was not solidified even by cooling to −20° C.

Example 3

Film Formation

A film was formed using the ruthenium complex (methyl type) obtained in Example 1 as a raw material by a bubbler method using a mass flow controller under the following conditions:
Vaporization temperature: 60° C.
Carrier gas: argon (500 sccm)
Chamber pressure: 266 Pa (2 torr)
Target material: $SiO_2$ wafer
Target material temperature: 270° C.
Film forming time: 5 min.

The formed ruthenium film was subjected to measurement of thickness and surface roughness with an FE-SEM. The thickness was 50 nm, and the surface roughness was 2 nm. The residual carbon concentration in the thin film was measured with a GD-MS. The residual carbon concentration was 20 to 30 ppm.

Example 4

Film Formation

A film was formed using the ruthenium complex (ethyl type) obtained in Example 2 as a raw material by a bubbler method using a mass flow controller under the following conditions:
Vaporization temperature: 70° C.
Carrier gas: argon (500 sccm)
Chamber pressure: 266 Pa (2 torr)
Target material: $SiO_2$ wafer
Target material temperature: 270° C.
Film forming time: 5 min.

The formed ruthenium film was subjected to measurement of thickness and surface roughness with an FE-SEM. The thickness was 50 nm, and the surface roughness was 2 nm. The residual carbon concentration in the thin film was measured with a GD-MS. The residual carbon concentration was 20 to 30 ppm.

It was revealed from the above-described results that the ruthenium complex of the present invention is obtained by a reaction between dodecacarbonyl triruthenium and a cyclooctatetraene derivative and that a satisfactory thin film can be produced by a chemical vapor deposition method using the complex as a raw material.

INDUSTRIAL APPLICABILITY

High-quality ruthenium thin film and ruthenium oxide thin film can be easily produced by using the ruthenium complex of the present invention. These thin films can be used for producing the capacitor electrode of a DRAM, resulting in increases in density and performance of the DRAM.

The invention claimed is:

1. A method of forming a film, comprising vaporizing a liquid form of a cyclooctatetraenetricarbonyl ruthenium complex as a raw material for producing a ruthenium film or a ruthenium oxide film by a chemical vapor deposition method, wherein the cyclooctatetraenetricarbonyl ruthenium complex is represented by General Formula (1):

[Formula 5]

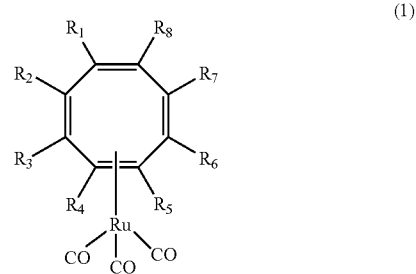

(1)

wherein one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms; and wherein the cyclooctatetraenetricarbonyl ruthenium complex is a liquid at 0° C.

2. The method of forming a film according to claim 1, wherein one of $R_1$, $R_2$, $R_3$, $R_4$, $R_5$, $R_6$, $R_7$, and $R_8$ of the General Formula (1) is a methyl group or an ethyl group, and the remaining are all hydrogen atoms.

3. The method of forming a film according to claim 1, further comprising producing the cyclooctatetraenetricarbonyl ruthenium complex of General Formula (1) by:
    irradiating a solution mixture of dodecacarbonyl triruthenium represented by the following Formula (2) and a cyclooctatetraene represented by the following Formula (3) with light having a wavelength of 300 to 850 nm:

[Formula 6]

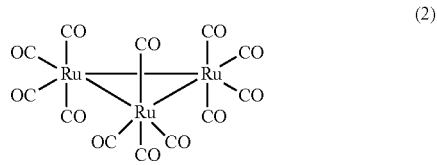

(2)

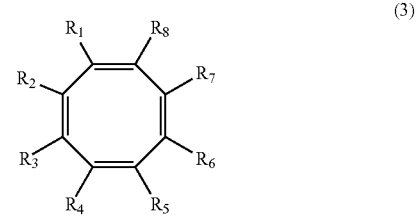

(3)

wherein one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms.

4. The method of forming a film according to claim 1, wherein the ruthenium film or the ruthenium oxide film is produced by thermally decomposing the ruthenium complex at 150 to 500° C.

5. The method of forming a film according to claim 1, wherein the ruthenium complex is vaporized at 10 to 150° C.

6. The method of forming a film according to claim 1, wherein the cyclooctatetraenetricarbonyl ruthenium complex is vaporized by bubbling a gas in to the liquid form of the ruthenium complex.

7. A method of forming a film, the method comprising:
vaporizing a liquid form of a cyclooctatetraenetricarbonyl ruthenium complex as a raw material;
depositing the vaporized material on to a substrate; and
thermally decomposing the deposited material to form a ruthenium film or a ruthenium oxide film on the substrate;
wherein the cyclooctatetraenetricarbonyl ruthenium complex is represented by General Formula (1):

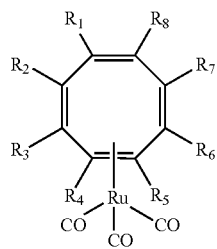

(1)

wherein one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms; and
wherein the cyclooctatetraenetricarbonyl ruthenium complex is a liquid at 0° C.

8. The method of forming a film according to claim 7, wherein the cyclooctatetraenetricarbonyl ruthenium complex is vaporized as a liquid at 10 to 150° C.

9. The method of claim 7, wherein the cyclooctatetraenetricarbonyl ruthenium complex is vaporized by bubbling a gas in to the liquid form of the ruthenium complex.

10. The method of forming a film according to claim 7, wherein one of $R_1$, $R_2$, $R_3$, $R_4$, $R_5$, $R_6$, $R_7$, and $R_8$ of the General Formula (1) is a methyl group or an ethyl group, and the remaining are all hydrogen atoms.

11. The method of forming a film according to claim 1, further comprising producing the cyclooctatetraenetricarbonyl ruthenium complex of General Formula (1) by:
irradiating a solution mixture between a temperature of 0° C. to 100° C. of dodecacarbonyl triruthenium represented by the following Formula (2) and a cyclooctatetraene represented by the following Formula (3) with light having a wavelength of 300 to 850 nm:

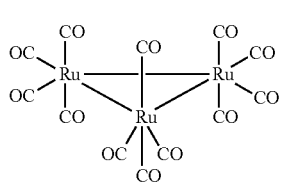

(2)

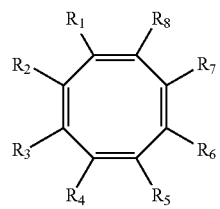

(3)

wherein one or two of $R_1$, $R_2$, $R_3$, $R_4$, $R_5$, $R_6$, $R_7$, and $R_8$ is or are each independently an alkyl group having 1 to 6 carbon atoms; the remaining are hydrogen atoms.

12. The method of forming a film according to claim 7, comprising thermally decomposing the deposited material at 150 to 500° C. to form the ruthenium film or the ruthen2ium oxide film on the substrate.

* * * * *